United States Patent
Cecchi

(10) Patent No.: US 10,426,754 B2
(45) Date of Patent: Oct. 1, 2019

(54) CRYSTALLINE FORM OF ANAVEX2-73 FOR THE TREATMENT OF ALZHEIMER'S DISEASE

(71) Applicant: Anavex Life Sciences Corp., New York, NY (US)

(72) Inventor: Marco Cecchi, Louisville, KY (US)

(73) Assignee: ANAVEX LIFE SCIENCES CORP., New York, NY (US)

( * ) Notice: Subject to any disclaimer, the term of this patent is extended or adjusted under 35 U.S.C. 154(b) by 0 days.

(21) Appl. No.: 15/622,588

(22) Filed: Jun. 14, 2017

(65) Prior Publication Data
US 2018/0360796 A1    Dec. 20, 2018

(51) Int. Cl.
| | |
|---|---|
| *A61K 31/341* | (2006.01) |
| *A61K 45/06* | (2006.01) |
| *A61K 31/13* | (2006.01) |
| *A61K 31/27* | (2006.01) |
| *A61K 31/445* | (2006.01) |
| *A61K 31/55* | (2006.01) |
| *A61K 9/00* | (2006.01) |

(52) U.S. Cl.
CPC ............ *A61K 31/341* (2013.01); *A61K 31/13* (2013.01); *A61K 31/27* (2013.01); *A61K 31/445* (2013.01); *A61K 31/55* (2013.01); *A61K 45/06* (2013.01); *A61K 9/0019* (2013.01)

(58) Field of Classification Search
CPC ...... A61K 9/14; A61K 9/0019; A61K 31/341; A61K 9/53
USPC ........................................................ 424/498
See application file for complete search history.

(56) References Cited

U.S. PATENT DOCUMENTS

2014/0296211 A1    10/2014  Vamvakides

FOREIGN PATENT DOCUMENTS

| WO | 97/30983 | 8/1997 |
| WO | 2014/155138 | 10/2014 |
| WO | 2017/013498 A2 | 1/2017 |

OTHER PUBLICATIONS

Author: Atsushi Kuriyama, et al. title: Assessment of Active Pharmaceutical Ingredient Particle Size in Tablets by Raman Chemical Imaging Validated using Polystyrene Microsphere Size Standards, AAPS PharmSciTech. Apr. 2014; 15(2): 375-387, Published online Jan. 11, 2014. (Year: 2014).*
International Search Report and Written Opinion dated Sep. 8, 2016 in corresponding International application PCT/US2016/042949.
"Phase IIa Study of Anavex2-73 Adaptive-Trial-Design with Repeated Doses, MTD Finding, Pharmacodynamic and Bioavailability Evaluation in Patients with Mild to Moderate Alzheimer's Disease with a 6-Month Open Label Follow-Up Period". ClinicalTrials.gov. Sep. 18, 2014.
Missling, Christopher. "The Anticpated Clinical Effect of the New Alzheimer Drug Anavex Plus in a Predictive Humanised Cortical Cognitive Model for Alzheimer's Disease". Clinical & Medical Research vol. 6, No. 1. Jan. 1, 2014.
Lahmy, Valentine, et al. "Blockade of Tau Hyperphosphorylation and A[beta]1-42 Generation by the Aminotetrahydrofuran Derivative Anavex2-73, a Mixed Muscarinic and [sigma]1 Receptor Agonist, in a Nontransgenic Mouse Model of Alzheimer's Disease". Neurophyschopharmacology, vol. 38, No. 9. Mar. 14, 2013.
Lahmy, Valentine, et al. "Mitochondrial Protection by the Mixed Muscarininc/[sigma]1 Ligand Anavex 2-73, a Tetrahydrofuran Derivative, in A[beta]25-35 Peptide-injected Mice, a Nontransgenic Alzheimer's Disease Model". Frontiers in Cellular Neuroscience, vol. 8. 2014.
Villad, Vanessa, et al. "Anti-amnesic and Neuroprotective Potentials of the Mixed Muscarinic Receptor/sigmal (.sigma.1) Ligand Anavex2-73, a Novel Aminotetrahydrofuran Derivative". Journal of Psychopharmacology, Oxford University Press, vol. 25, No. 8. Jan. 1, 2011.
Mason, V.L. "Alzheimer's Association International Conference on Alzheimer's Disease 2015". Drugs of Today, vol. 51, No. 7. Jul. 22, 2015.
International Search Report and Written Opinion dated May 9, 2018 in International application PCT/US2017/037436 ; 30 pages.
MacFarlane et al., "New exploratory Alzheimer's drug anavex 2-74 changes in electrophysiological markers in Alzheimer's disease: First patient data from an ongoing Phase 2a study in mild-to-moderate Alzheimer's patients," Alzheimer's & Dementia: The Journal of the Alzheimer's Associate, 2015, vol. 11, No. 7, 1 page.
MacFarlane et al., "Safety and efficacy at 31 weeks of Anavex 2-73 in a Phase 2a study in mild-to-moderate Alzheimer's Disease patients," Alzheimer's & Dementia: The Journal of the Alzheimer's Associate, 2016, vol. 12, No. 7, 1 page.

* cited by examiner

*Primary Examiner* — Yanzhi Zhang
(74) *Attorney, Agent, or Firm* — Tara A. Nealey; Polsinelli PC

(57) ABSTRACT

Composition and method for treatment of Alzheimer's disease that includes ANAVEX2-73. Method of treatment of Alzheimer's disease using pharmaceutical compositions comprising ANAVEX2-73 according to an intermittent dosage regimen.

25 Claims, 14 Drawing Sheets

CRYSTALLINE FORM OF ANAVEX2-73 FOR THE TREATMENT OF ALZHEIMER'S DISEASE

FIELD

The present disclosure relates to pharmaceutical compounds and compositions for the treatment of Alzheimer's disease. In particular, the present disclosure relates to the use of pharmaceutical compositions comprising ANAVEX2-73 (also A2-73) for the treatment of Alzheimer's disease.

BACKGROUND

Despite major efforts aimed at finding a treatment for Alzheimer's disease, progress in developing compounds that can relieve cognitive deficits associated with the disease has been slow. ANAVEX2-73 or A-273 (tetrahydro-N,N-dimethyl-2,2-diphenyl-3-furanmethanamine hydrochloride) is a compound which is believed to bind to sigma-1 and muscarinic acetylcholine receptors with affinities in the low micromolar range. ANAVEX2-73 has the chemical structure:

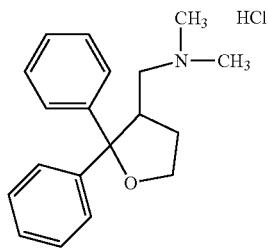 [SMILES: Cl ; CN(C)CC1CCOC1(c1ccccc1)c1ccccc1]

The sigma-1 receptor is a chaperone protein in the endoplasmic reticulum (ER) that chaperones the IP3 receptor at the ER and mitochondrion interface to ensure proper $Ca^{2+}$ signaling from the ER into the mitochondrion. Under pathological conditions in which cells encounter stress that results in the ER losing its global $Ca^{2+}$ homeostasis, the sigma-1 receptor translocates and counteracts the arising apoptosis. As a result, the sigma-1 receptor is a receptor chaperone essential for the metabotropic receptor signaling and for the survival against cellular stress. See Centr. Nerv. Syst. Agents Med. Chem. 9(3), 184-189 (2009).

It has been reported that ANAVEX2-73 showed neuroprotective potential against amyloid toxicity in mice. In particular, ANAVEX2-73 has been reported as attenuating oxidative stress, caspases induction, cellular loss and learning and memory deficits observed in mice one week after the i.c.v. injection of an oligomeric preparation of amyloid $\beta_{25-35}$ peptide ($A\beta_{25-35}$). See J. Psychopharmacol. 25(8), 1101-1117 (2011). More recently, it has been reported that ANAVEX2-73 blocked the $A\beta_{25-35}$-induced P-Akt decrease and P-GSK-3β increase, indicating activation at the PI3K neuroprotective pathway. See *Neuropsychopharmacology* 38, 1706-1723 (2013). In the dose-range tested, ANAVEX2-73 attenuated the hyperphosphorylation of Tau on physiological epitopes (AT-8 antibody clone) and on pathological epitopes (AT-100 clone). ANAVEX2-73 also has been reported to decrease the $A\beta_{25-35}$-induced endogenous $A\beta_{1-42}$ seeding.

Reference is made to U.S. Patent Publication No. 2014/0296211 entitled "ANAVEX2-73 AND CERTAIN ANTI-CHOLINESTERASE INHIBITORS COMPOSITION AND METHOD FOR NEUROPROTECTION," to Vamvakides et al., filed Jul. 12, 2013; U.S. Ser. No. 62/065,833 entitled "A19-144, A2-73 AND CERTAIN ANTICHOLINESTERASE INHIBITOR COMPOSITIONS AND METHOD FOR ANTI-SEIZURE THERAPY," filed Oct. 20, 2014; U.S. Patent application entitled "CRYSTAL FORMS OF TETRAHYDRO-N,N-DIMETHYL-2,2-DIPHENYL-3-FURANMETHANAMINE HYDROCHLORIDE, PROCESSES OF MAKING SUCH FORMS, AND THEIR PHARMACEUTICAL COMPOSITIONS" and filed on date even herewith; U.S. Patent application entitled "ENANTIOMERS OF A2-73, ANALOGUES, AND SIGMA AGONIST ACTIVITY" and filed on date even herewith. The teaching of these applications and publications and all references cited herein are incorporated by reference in their entirety.

SUMMARY OF THE PRESENT DISCLOSURE

The present disclosure comprises a pharmaceutical composition for the treatment of Alzheimer's disease comprising a therapeutically effective amount of ANAVEX2-73. Particular reference is made to treatment with the composition wherein the Alzheimer's disease is mild-to-moderate, and more particularly wherein the ANAVEX2-73 is characterized by the PXRD pattern shown in FIG. 1 as well as characterized by the thermogravimetric analysis of FIG. 2a or FIG. 2b and characterized by the differential scanning calorimetry analysis of FIG. 3a, 3b, or 3c.

Further included is the pharmaceutical composition wherein the ANAVEX2-73 is characterized by the particle shapes or sizes as depicted in FIG. 4a, FIG. 4b, or FIG. 4c. Specific reference is made to a particle size of between 1 and 50 μm.

Noted therapeutically effective amount of ANAVEX2-73 include about 1 mg to about 60 mg and particularly about 30 mg to about 50 mg. Further noted are therapeutically effective amounts of about 3 mg to about 5 mg, and particularly for intravenous administration. Oral dosage forms are noted.

Yet further included are combination dosages comprising at least one acetylcholinesterase inhibitor with particular reference to donepezil, galantamine, rivastigmine, or memantine.

The present disclosure contemplates a method of treating Alzheimer's disease in a subject comprising administering to the subject a pharmaceutical compositions and combinations noted above.

Contemplated dosage regimens include administering to the subject a pharmaceutical composition comprising ANAVEX2-73 according to an intermittent dosing regimen of at least two cycles, each cycle comprising (a) a dosing period during which a therapeutically effective amount of said pharmaceutical composition is administered to said patient and, thereafter, (b) a resting period. In some embodiments the dosing period and the resting period are of the same duration or are of different durations.

Attention is brought to the dosing period and the resting period in the range of a lower limit of about 1 day, 2 days, 3 days, 4 days, 5 days, 6 days, 7 days, 8 days, 9 days, 10 days, 11 days, 12 days, 13 days, and 14 days to an upper limit of about 28 days, 27 days, 26 days, 25 days, 24 days, 23 days, 22 days, 21 days, 20 days, 19, days, 18 days, 17 days, 16 days, 15 days, and 14 days. Also noted is the dosing period of between about 1 day and 12 days and the resting period is between about 1 day and 12 days with particular reference to a dosing period is 12 days and resting period is 12 days. Such regimen is usefully employed wherein the therapeutically effective amount of said pharmaceutical composition of ANAVEX2-73 is about 1 mg to about 60 mg and particularly about 30 mg to about 50 mg, and particularly for oral dosage forms. Also contemplated are ANAVEX2-73 dosages of about 3 mg to about 5 mg and particularly with intravenous administration.

BRIEF DESCRIPTION OF THE DRAWINGS

In order to describe the manner in which the advantages and features of the disclosure can be obtained, reference is made to embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure.

It should be understood at the outset that although illustrative implementations of one or more embodiments are illustrated below, the disclosed method may be implemented using any number of techniques. The disclosure should in no way be limited to the illustrative implementations, drawings, and techniques illustrated herein, but may be modified within the scope of the appended claims along with their full scope of equivalents.

In the following discussion and in the claims, the terms "including" and "comprising" are used in an open-ended fashion, and thus should be interpreted to mean "including, but not limited to . . . ". The various characteristics described in more detail below, will be readily apparent to those skilled in the art with the aid of this disclosure upon reading the following detailed description, and by referring to the accompanying drawings.

The present disclosure generally relates to pharmaceutical compounds and compositions for the treatment of Alzheimer's disease. More particularly, the present disclosure relates to the use of pharmaceutical compositions containing ANAVEX2-73 for the treatment of Alzheimer's disease.

According to an embodiment of the present disclosure, ANAVEX2-73 can be produced by charging a solution of tetrahydro-N,N-dimethyl-2,2-diphenyl-3-furanmethanamine free base in ethyl acetate with isopropanol. The ethylacetate is removed by distillation and the remaining isopropanol solution containing tetrahydro-N,N-dimethyl-2,2-diphenyl-3-furanmethanamine free base is clear filtered. Aqueous hydrochloric acid (1.1 eq) is charged to the isopropanol solution and the formed crystalline HCl salt of tetrahydro-N,N-dimethyl-2,2-diphenyl-3-furanmethanamine, tetrahydro-N,N-dimethyl-2,2-diphenyl-3-furanmethanamine hydrochloride (ANAVEX2-73), is isolated by filtration and dried under vacuum at 55° C. for 3 days. The ANAVEX 2-73, thus obtained, is characterized by powder X-ray diffraction (PXRD), thermogravimetric analysis (TGA), differential scanning calorimetry (DSC), and scanning electron microscopy (SEM), as shown in FIGS. 1-4.

Figure 1:
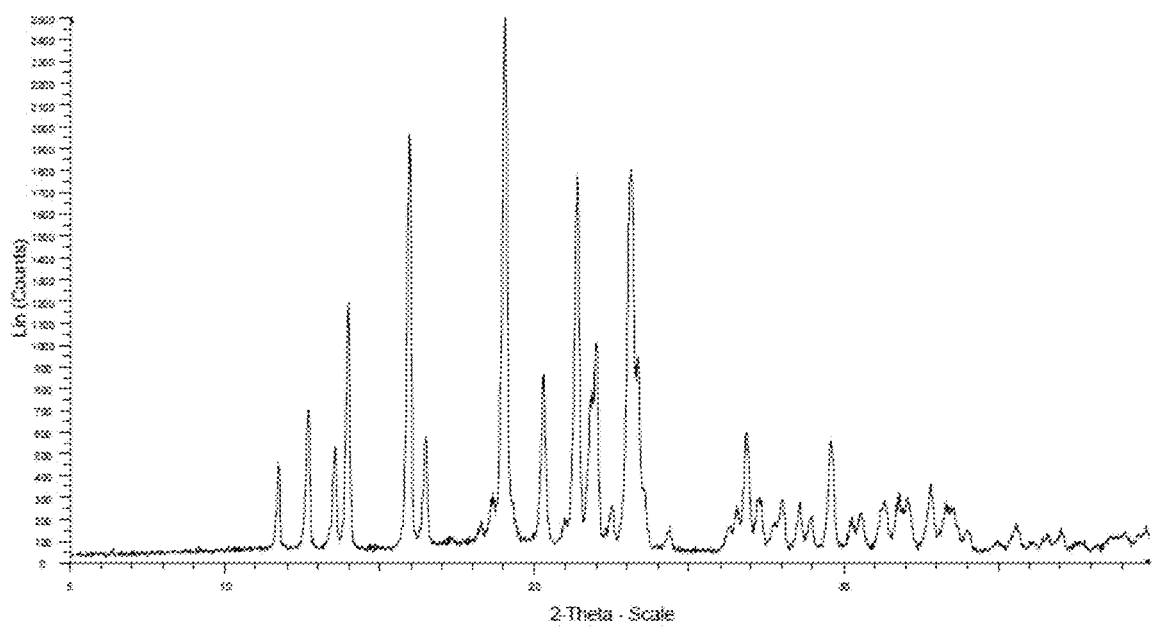
FIG. 1 depicts a powder X-ray diffraction (PXRD) pattern of ANAVEX2-73, according to an embodiment of the present disclosure.

FIG. 1 depicts a powder X-ray diffraction (PXRD) pattern for ANAVEX2-73, according to an embodiment of the present disclosure. The PXRD pattern shown in FIG. 1 was collected using a Siemens D5000 powder diffractometer with CuKα radiation (1.54056 Å). The tube voltage and amperage were set at 40 kV and 40 mA, respectively. The divergence slit and antiscattering slit settings were variable for the illumination on the 20 mm sample area. Each sample was scanned between 5° and 40° in 2θ with a step size of 0.02°. The measurement time per step was 2 seconds. The instrument was previously calibrated using a silicon standard. As shown in FIG. 1, the PXRD indicates that the ANAVEX2-73 material is highly crystalline with several characteristic peaks in the 10-20° 2θ range.

Figure 2A:
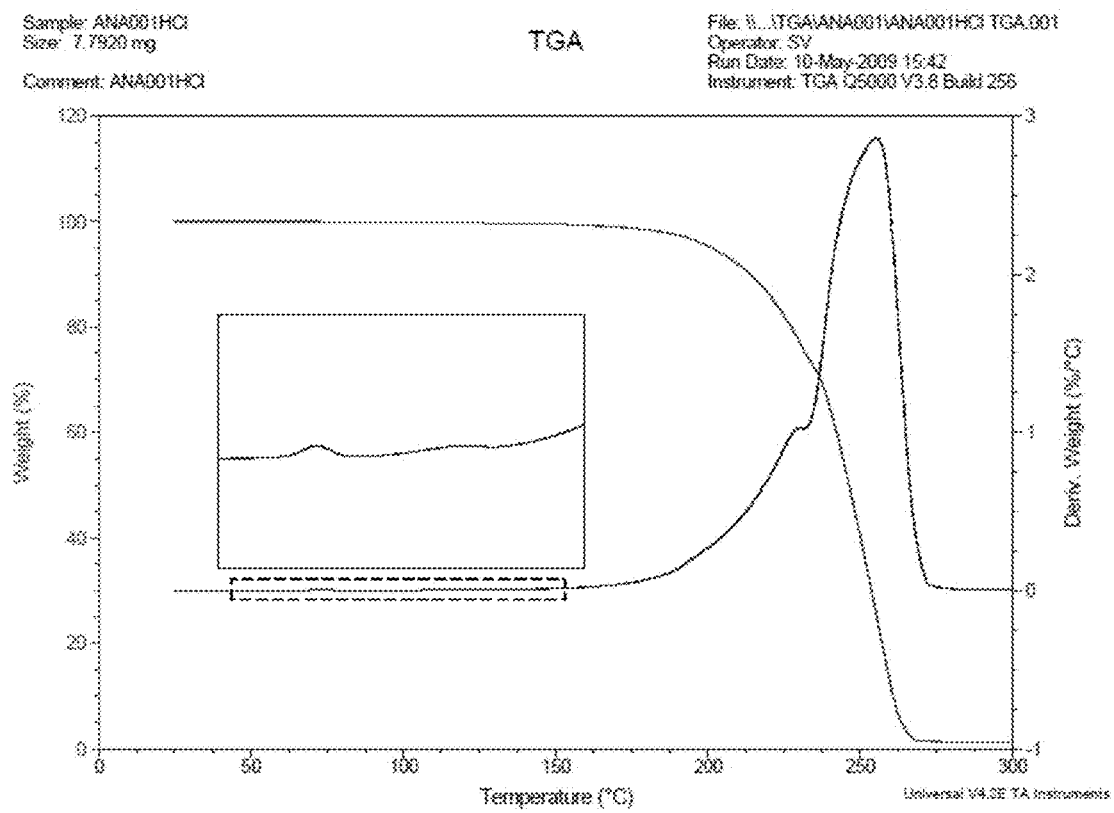
FIG. 2a depicts a thermogravimetric analysis (TGA) of ANAVEX2-73, according to an embodiment of the present disclosure.
Figure 2B:
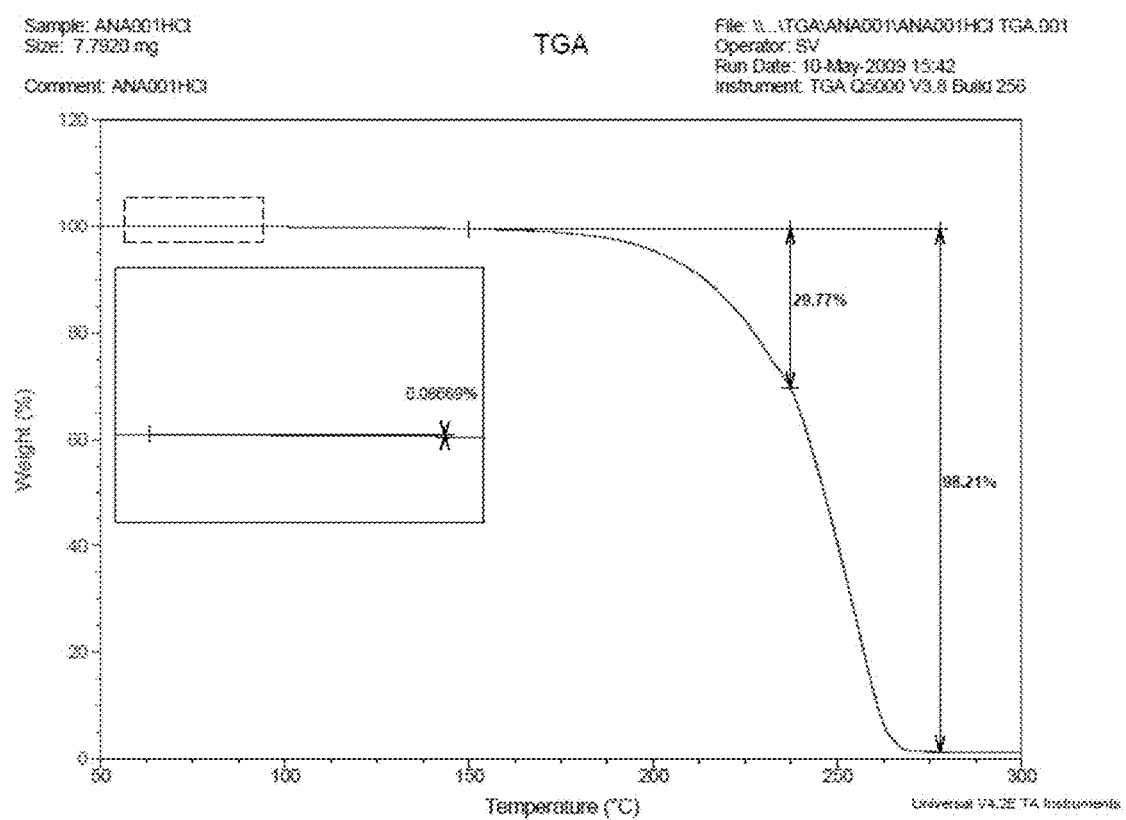
FIG. 2b depicts a thermogravimetric analysis (TGA) of ANAVEX2-73, according to an embodiment of the present disclosure.

FIGS. 2a and 2b depict thermogravimetric analysis (TGA) data for ANAVEX2-73, according to an embodiment of the present disclosure. The weight loss of the sample as a function of temperature was measured using the Thermal Advantage TGA Q5000IR (TA instrument) module. The samples (~7.8 mg) was placed onto the platinum pan (100 μL) and heated from 25°-350° at a heating rate of 10° C./min under nitrogen purge. As shown in FIGS. 2a-2b, the TGA (and derivative of weight change) curves indicate that the minor weight change at around 80° C. followed by continuous weight loss from 150° C. with two major steps (first one with ~29% at 228° C.) up to 275° C. The initial weight loss could be attributed to the evaporation of adsorbed water or solvent of crystallization and the latter weight changes may be attributed to the degradation of impure solid phases (or impurities) followed by a melt-degradation of ANAVEX2-73.

Figure 3A:
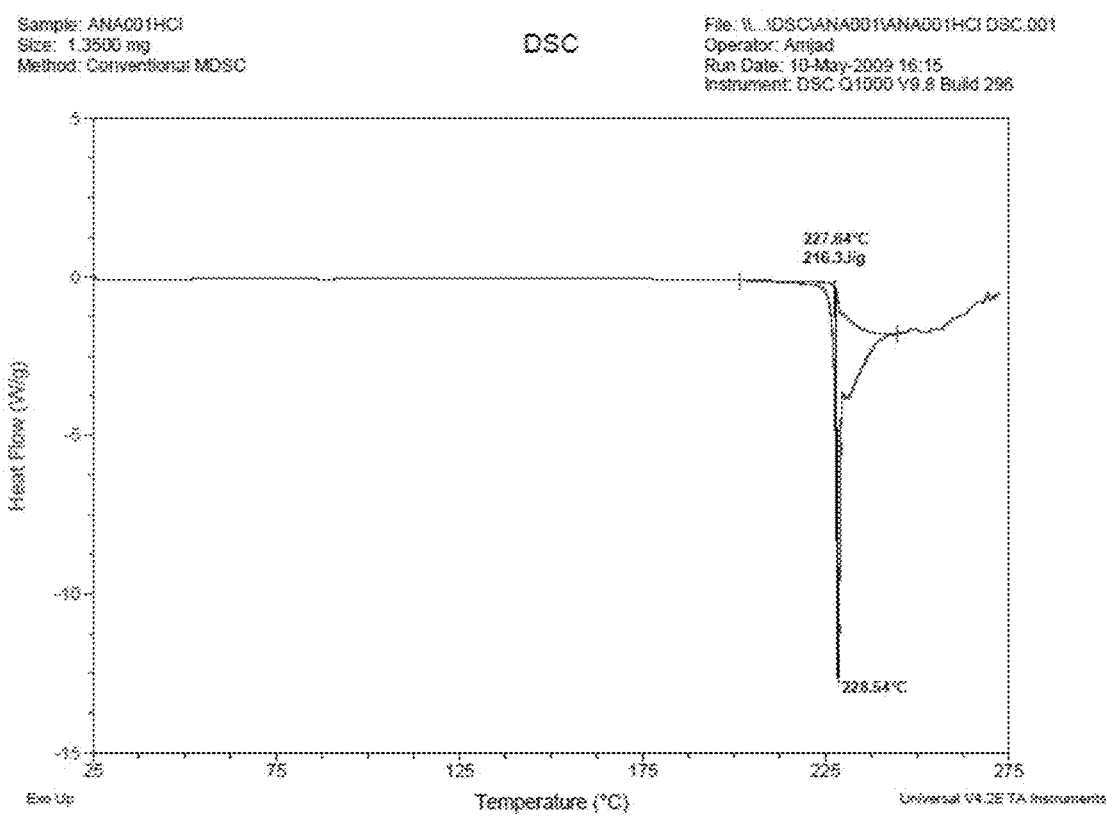
FIG. 3a depicts differential scanning calorimetry (DSC) analysis data for ANAVEX2-73, according to an embodiment of the present disclosure.
Figure 3B:
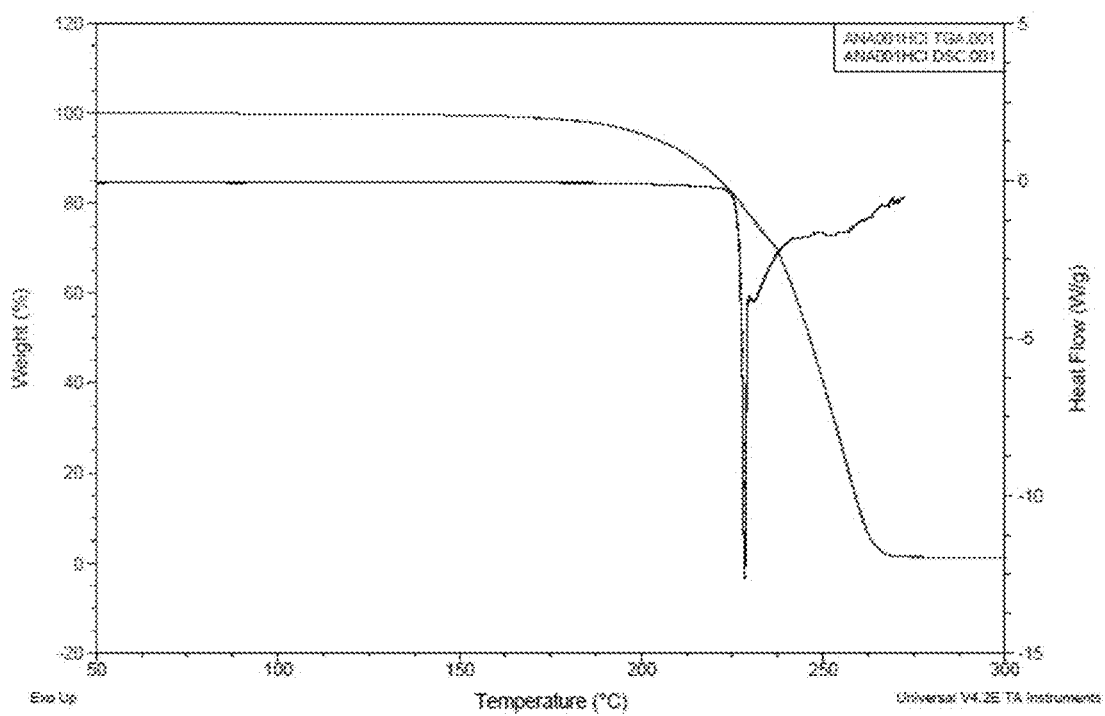
FIG. 3b depicts differential scanning calorimetry (DSC) analysis data for ANAVEX2-73, according to an embodiment of the present disclosure.
Figure 3C:
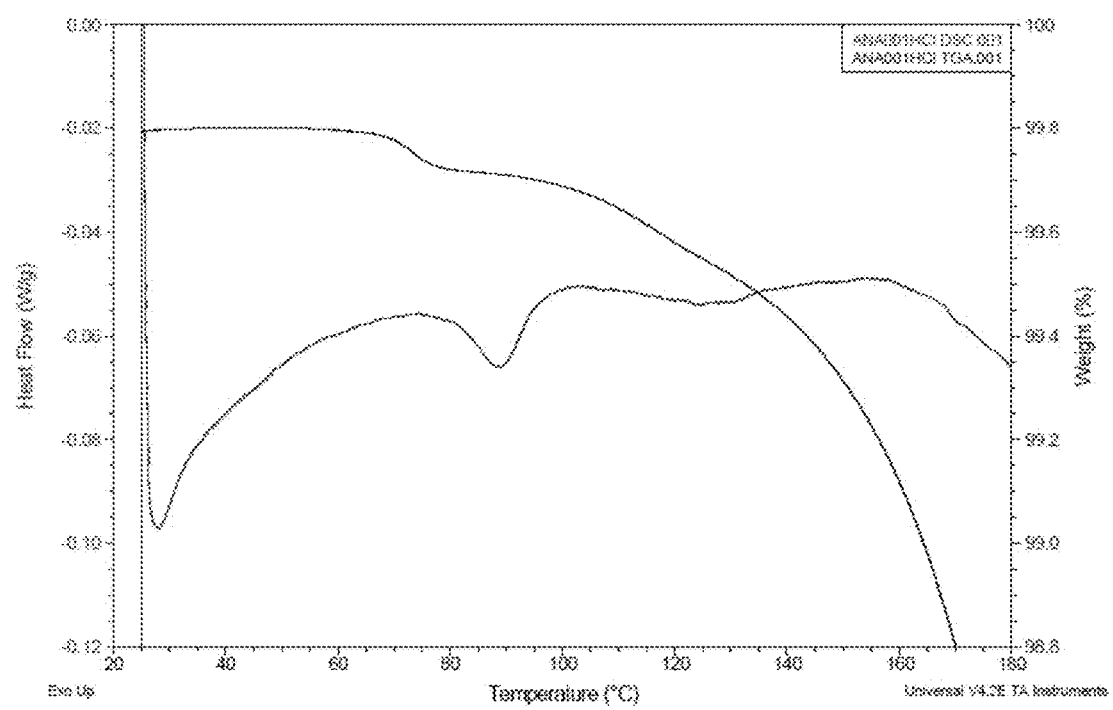
FIG. 3c depicts differential scanning calorimetry (DSC) analysis data for ANAVEX2-73, according to an embodiment of the present disclosure.

FIGS. 3a, 3b, and 3c depict differential scanning calorimetry (DSC) data for ANAVEX2-73, according to an embodiment of the present disclosure. The thermal behavior of ANAVEX2-73 was studied using a Thermal Advantage DSC Q1000 (TA instruments) equipped with a refrigerated cooling system. The instrument had been calibrated for temperature and enthalpy using indium. 1-2 mg of the sample was accurately weighed into a non-hermetic aluminum pan and crimped. The sample was scanned from 25° C. to 275° C. at a heating rate of 10° C./min under continuous nitrogen purge (50 mL/min). As shown in FIGS. 3a-3c, the DSC thermograms indicate endothermic events with onset at ~80° C. (minor) and 115° C. (broad) followed by an exothermic peak and a sharp endothermic event with onset at 227° C. DSC analysis seemed to be in agreement with the TGA analysis suggesting that the compound was undergoing melt-degradation. However, start of the degradation of the main phase in the vicinity but before the melting is also possible.

Figure 4A:
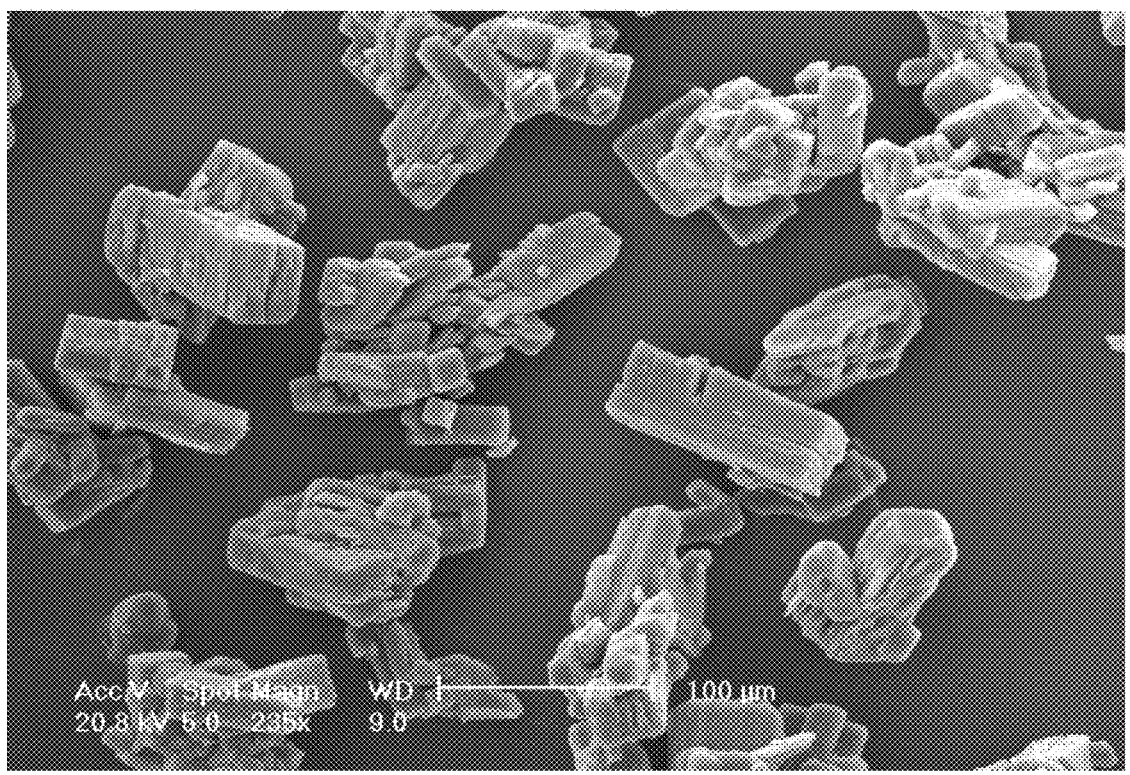
FIG. 4a depicts an SEM micrograph demonstrating the size and morphology of the particles of ANAVEX2-73, according to an embodiment of the present disclosure.
Figure 4B:
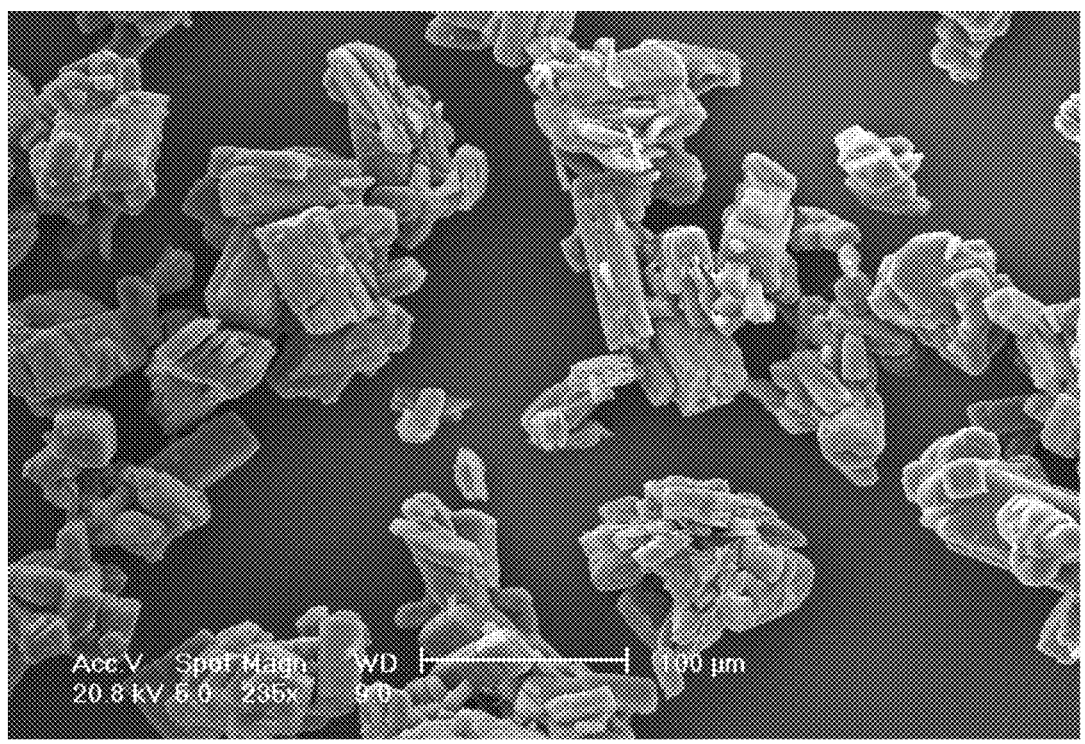
FIG. 4b depicts an SEM micrograph demonstrating the size and morphology of the particles of ANAVEX2-73, according to an embodiment of the present disclosure.
Figure 4C:
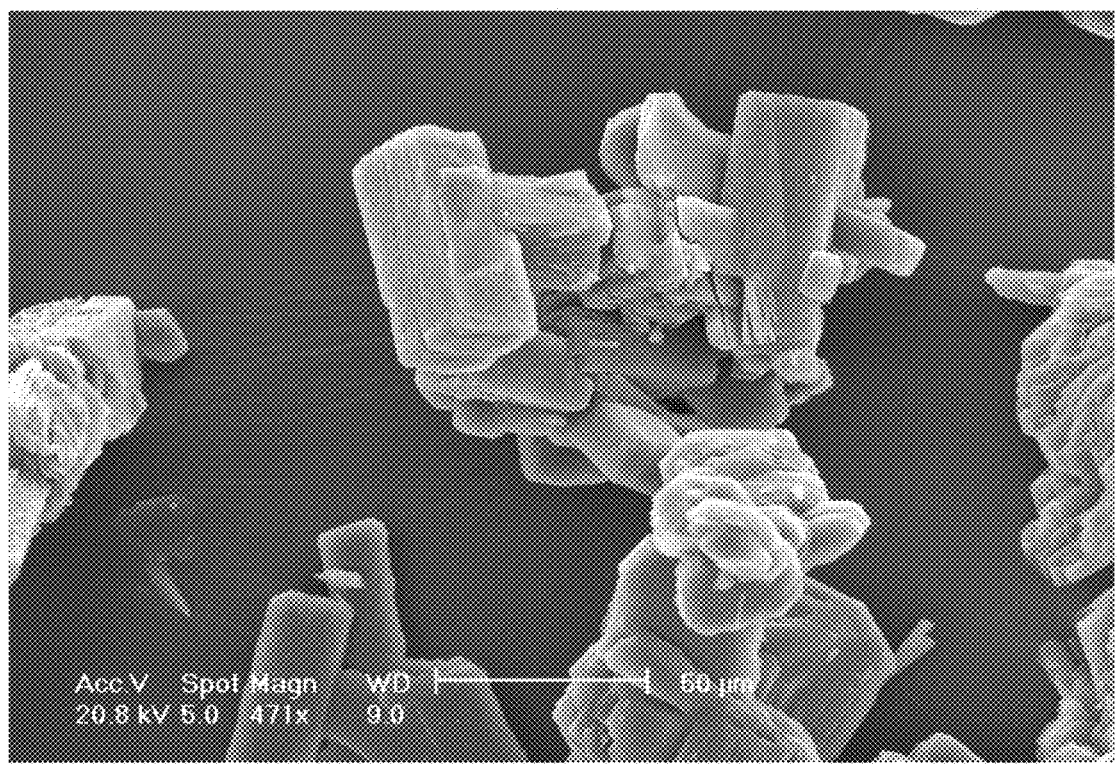
FIG. 4c depicts an SEM micrograph demonstrating the size and morphology of the particles of ANAVEX2-73, according to an embodiment of the present disclosure.

FIGS. 4a, 4b, and 4c depict scanning electron microscope (SEM) micrographs demonstrating the size and morphology of the particles of ANAVEX2-73, according to an embodiment of the present disclosure. The size and morphology of the particles was studied using a Philips XL30 (The Netherlands) scanning electron microscope (SEM). The samples were sprinkled onto double-sided tape that had been secured onto an aluminum stub and then gold sputter-coated at mA for 40 seconds under an argon atmosphere. The particles were analyzed at suitable acceleration voltages and magnifications. Representative micrographs were taken and the particle size was estimated. The SEM micrographs demonstrated that ANAVEX2-73 is primarily comprised of aggregated crystals (prisms to blocks) with a primary particle size distribution between 1 and 50 μm.

The safety of ANAVEX2-73 has been demonstrated in a randomized, placebo-controlled single ascending dose Phase 1 study of ANAVEX2-73 in 22 healthy male volunteers. See Poster: A Phase 1 Dose Escalation Study to Investigate Safety, Tolerability, and Pharmacokinetics of ANAVEX2-73 in Healthy Male Subjects, CNS Summit 2014, Boca Raton, Fla., by Ole Voges, Ingo Weigmann, Norman Bitterlich, Christoph Schindler and Christopher Missling. Ascending single oral doses of 1 mg, 10 mg, 30 mg, 40 mg, 50 mg, and 55 mg of ANAVEX2-73 were safe and well tolerated in healthy subjects. No serious adverse events occurred. Based on the frequency and intensity of non-treatment emergent adverse events (TEAEs) the maximum tolerable dose (MTD) and the minimum intolerable dose (MID) were defined as 55 mg and 60 mg, respectively. A highest doses, observed adverse events included moderate and reversible dizziness and headache, common in drugs that target the central nervous system. Blood pressure and resting heart rate and other clinical parameters such as vital signs and 12-lead electrocardiogram (ECG) did not show any clinically relevant or dose-dependent changes. The QT interval and QTcB also did not reveal any clinically significant changes. The pharmacokinetics of ANAVEX2-73 was found to be suitable for daily oral dosing.

The efficacy of ANAVEX2-73 polymorph for the treatment of Alzheimer's disease has been demonstrated by initial clinical data from an on-going Phase 2a clinical trial. The 36-day multicenter randomized clinical trial included both male and female mild-to-moderate Alzheimer's disease patients. ANAVEX2-73 was administered to twelve subjects as an add-on therapy to the donepezil current standard of care. ANAVEX2-73 was administered according to a two-period on-off-on cross-over dosing regimen in which the subjects were administered ANAVEX2-73 for 12 days ($1^{st}$ period) followed by a 12-day wash-out period before being administered ANAVEX2-73 for a second 12-day period ($2^{nd}$ period). Those subjects that were administered ANAVEX2-73 by oral administration during the $1^{st}$ period were administered ANAVEX2-73 intravenously during the $2^{nd}$ period, and vice versa. About half of the subjects were administered a 30 mg oral dosage form while the other half of subjects were administered a 50 mg oral dosage form. The intravenous dosage was either 3 mg or 5 mg, with about half of the subjects administered 3 mg and the other half administered 5 mg.

Resting electroencephalographic (EEG) activity and event related potentials (EEG/ERP) were used to assess the cognitive effects of ANAVEX2-73 administration. Event related potentials (ERPs) are voltage changes time-locked to some physical or mental occurrence in ongoing electrical brain activity, as recorded by EEG. Event-related potentials (ERPs) provide a sensitive and reliable measure of the cognitive effects associated with early Alzheimer's disease. ERPs reflect well characterized brain responses to sensor, motor and cognitive events and have been found to be altered in Alzheimer disease patients beginning in the very early stages of the disease. See for example, New Encycl. Neurosci., Oxford Academic Press, p. 13-18 (2009). For example, ERP tests on young presymptomatic individuals who carry mutations in the presenilin-1 and amyloid precursor protein genes show significant changes in ERP patterns years before the onset of behavioral symptoms and the development of Alzheimer's disease. See for example, *Neurology* 73, 1649-1655 (2009); *Neurology* 77, 469-475 (2011). ERPs have also been shown to reliably track the cognitive decline associated with Alzheimer's disease progression. For instance, ERP markers of cognitive function are increasingly altered in longitudinal studies on individuals with mild cognitive impairment (MCI) and Alzheimer's disease patients. See for example, *Clin. Neurophysiol.* 122, 1322-1326 (2011); *Clin. Neurophysiol.* 121, 194-199 (2010). Additionally, ERPs have been shown to be sensitive to the effects of cognitive enhancers currently used for the treatment of Alzheimer's disease. For example, ERP measures have been demonstrated to be reliable instruments for the assessment of the cognitive response to cholinesterase inhibitors, such as donepezil, and the effects of the selective NMDA antagonist memantine, as measured by ERPs, have been shown to correlate with changes in the Mini Mental State Examination (MMSE) score. See for example, *Neurol. Neurochir. Pol.* 35 Suppl 3, 37-43 (2001); *Clin. Neuropharmacol.* 25, 207-215 (2002); *Neurosci. Biomed. Eng.* 1, 34-39 (2013).

In particular, the auditory P300 component of the ERP has been widely applied in the study of age-related cognitive dysfunction because it is thought to reflect attentional and memory processes. Auditory P300 is a positive deflection occurring at about 300 ms from stimulus onset. It is generated by the activation of multiple neocortical and limbic regions. Auditory P300 has two functionally different components, an earlier P3a component that is maximal over frontocentral regions, and a later P3b component (hereafter "P300") that is maximal at the posterior scalp locations. See for example, *Int. J. of Alzheimer's Dis.* 2011, Article ID 653173, 1-7 (2011). P300 amplitude data collected as part of a double blind six month study for 15 patients with mild Alzheimer's disease on donepezil, as compared to a vitamin E baseline, has shown that P300 amplitude data correlates with ADAS-Cog and MMSE data for the same patients. See, *Clin. Neuropharmacol.* 25(4), 207-215 (2002).

Subjects were tested using a three-stimulus oddball paradigm. Stimuli comprised of standard tones (1000 Hz), target tones (2000 Hz) and unexpected distractor tones (white noise) that were played with probabilities of 0.75, 0.15, and 0.10. Tones were presented in pseudorandom order, so that target and distractor tones were never presented sequentially. Subjects were instructed to respond to the target stimuli by pressing a button with their dominant hand. For each test, between 300 and 400 stimuli were presented binaurally through insert ear phones at 70 dB volume. The tone duration for each stimulus was 100 ms with rise and fall times of 10 ms. The interstimulus interval was randomized between 1.5 and 2 s. Electroencephalographic (EEG) activity was recorded from seven electrode sites (Fz, Cz, Pz, F3, P3, F4, and P4) of the international 10-20 system using a COGNISION™ Headset (Neuronetrix). Electrodes were referenced to averaged mastoids (M1, M2) and Fpz served as the common electrode. The headset used for data collection had been validated to perform reliable ERP recordings when skin contact impedance was below 70 kΩ. Impedance was automatically checked at all electrodes after each target or distractor tone, and was kept below this limit throughout each test. Data was collected from −240 to 1,000 ms around the stimuli, digitized at 125 Hz, and bandpass filtered from 0.3 to 35 Hz. An automatic artifact threshold detection limit of ±100 µV was set for the tests. Trial sets of a deviant tone and the immediately preceding standard tones (epoch sets) with artifacts exceeding the threshold were rejected in real time and immediately repeated.

Figure 5:
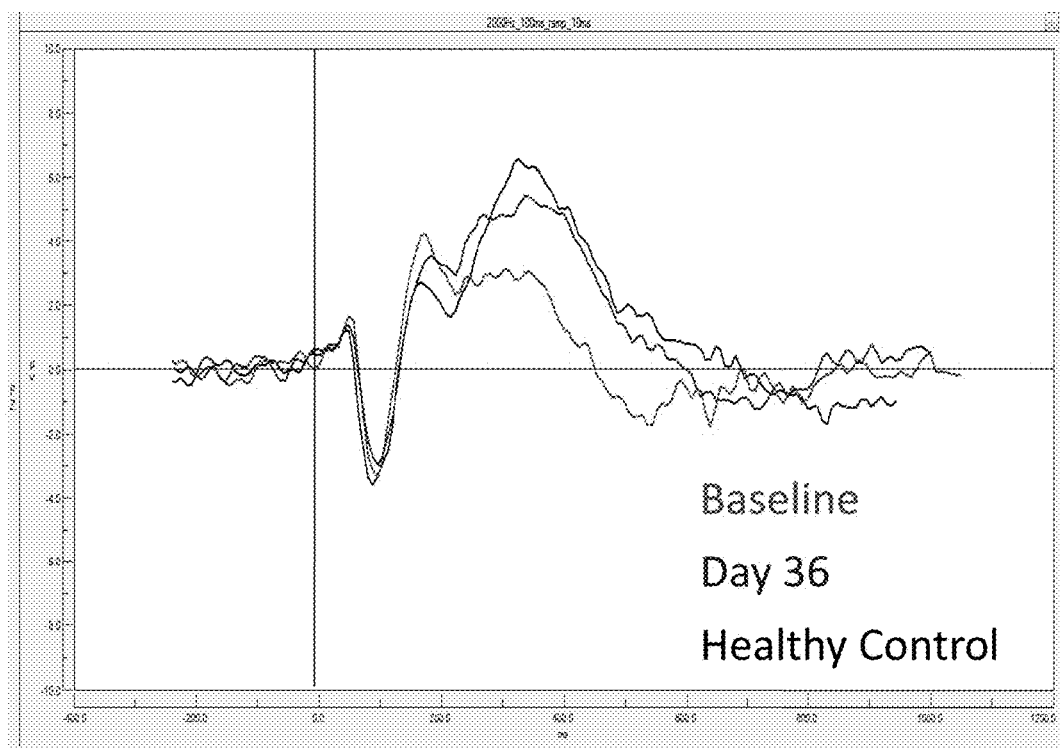
FIG. 5 is a plot illustrating P300 ERP wave data for twelve patients at baseline and day 36 following the on-off-on ANAVEX2-73 dosing regimen, as compared to a healthy control group.

FIG. 5 illustrates P300 ERP wave data for twelve patients at baseline and day 36 following the on-off-on ANAVEX2-73 dosing regimen, without any dose optimization. FIG. 5 also illustrates data for a healthy control group obtained from a manuscript that was recently submitted by Cecchi et al. to the journal *Alzheimer's & Dementia*. The P300 ERP wave data indicates that administration of ANAVEX2-73 improved measured cognitive performance as compared to the baseline data. Additionally, the P300 ERP wave plot for subjects undergoing the ANAVEX2-73 dosage regimen more closely resembled the P300 ERP wave plot obtained for healthy subjects.

Figure 6:
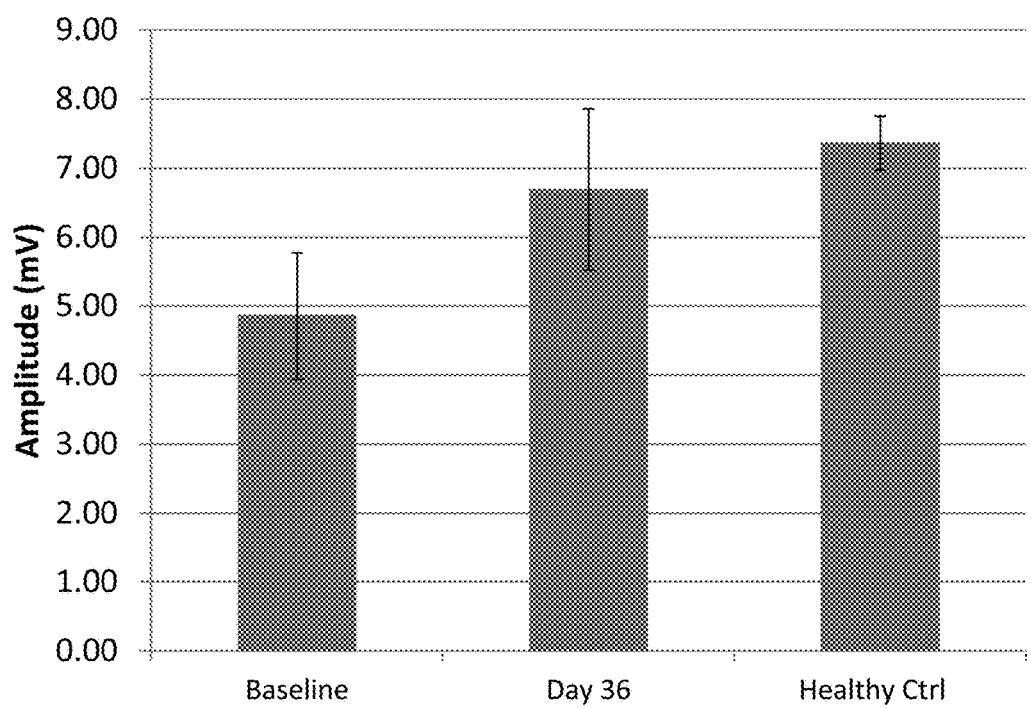
FIG. 6 illustrates P300 amplitude data for twelve patients at baseline and day 36 following the on-off-on ANAVEX2-73 dosing regimen, as compared to a healthy control group.

FIG. 6 illustrates P300 amplitude data for twelve patients at baseline and day 36 following the on-off-on ANAVEX2-73 dosing regimen, as compared to the healthy control group. The same data is provided in Table 1. As shown in Table 1, the P300 amplitude for subjects undergoing the ANAVEX2-73 dosage regimen increased by 38% as compared to the baseline P300 amplitude. Additionally, the P300 amplitude for subjects undergoing the ANAVEX2-73 dosage regimen more closely resembled the P300 amplitude data obtained for the healthy control group than the baseline P300 amplitude data.

TABLE 1

|  | P300 Amplitude (mV) | Percentage Increase Over Baseline Data |
|---|---|---|
| Baseline | 4.85 | 0% |
| Day 36 | 6.69 | 38% |
| Healthy Ctrl | 7.36 |  |

Table 2 demonstrates the effects of the ANAVEX2-73 dosage regimen on the cognitive performance of the twelve subjects at baseline and day 36 following the on-off-on ANAVEX2-73 dosing regimen, as measured by the target detection task of the ERP test. Table 2 also provides target detection task data for the healthy control group. As shown in Table 2, the button press accuracy was improved for subjects undergoing the ANAVEX2-73 dosage regimen as compared to the baseline. Additionally, the median reaction time and the false alarm percentage was reduced for the ANAVEX2-73 administered subjects as compared to the baseline. The healthy control group out-performed the day 36 ANAVEX2-73 subjects in button press accuracy and median reaction time. However, the day 36 ANAVEX2-73 subjects out-performed the healthy control group in false alarm percentage. The data provided in Table 2 indicates that ANAVEX2-73 administration improves both the accuracy and the reaction time of subjects performing the target detection task of the ERP test.

TABLE 2

| Target Detection Task | Baseline | Day 36 | Healthy Control |
|---|---|---|---|
| Button Press Accuracy (%) | 86.2 ± 4.47 | 87.5 ± 4.01 | 94.1 ± 1.10 |
| False Alarms (%) | 2.67 ± 1.12 | 0.64 ± 0.26 | 1.10 ± 0.20 |
| Median Reaction Time (ms) | 593 ± 33.0 | 534 ± 42.0 | 458 ± 11.4 |

Figure 7:
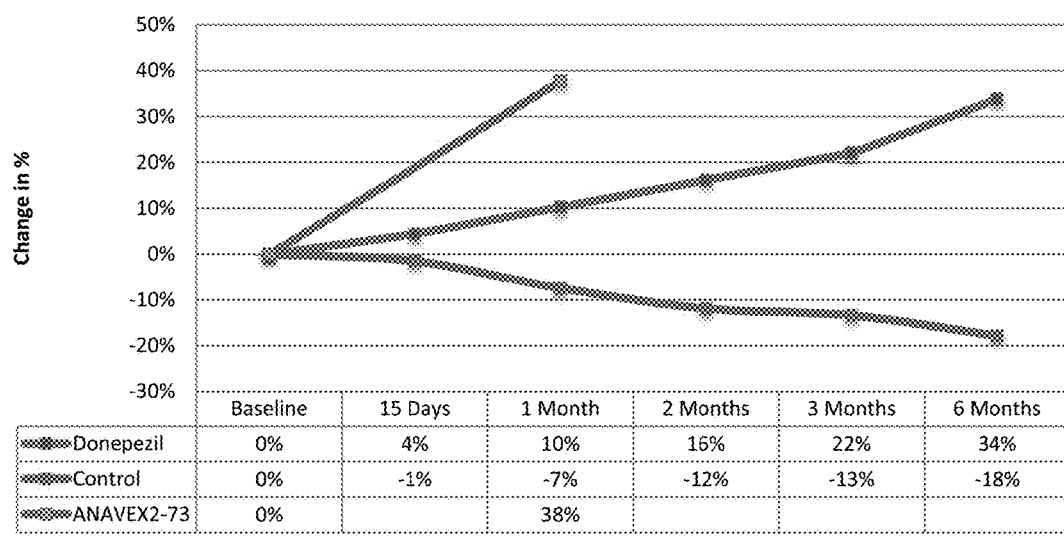
FIG. 7 illustrates P300 amplitude data for twelve patients at day 36 (1 month) following the on-off-on ANAVEX2-73 dosing regimen, as compared to historical donepezil and control data.

FIG. 7 illustrates P300 amplitude data for twelve patients at day 36 (1 month) following the on-off-on ANAVEX2-73 dosing regimen, as compared to historical donepezil and control data obtained from *Clin. Neuropharmacol.* 25(4), 207-215 (2002). As shown in FIG. 7, the measured P300 amplitude change for subjects undergoing the ANAVEX2-73 dosage regimen, as compared to the baseline P300 amplitude, is about four times higher than the P300 amplitude change observed in historical data for patients administered donepezil at the 1 month time point. Further, the percent P300 amplitude change after 1 month is greater than the percent P300 amplitude change observed in historical data for patients administered donepezil after 6 months. The data shown in FIG. 7 suggests that administration of ANAVEX2-73 increases measured P300 amplitude for subjects at an earlier time point in the dosage regimen and to a greater degree than administration of donepezil.

Figure 8:
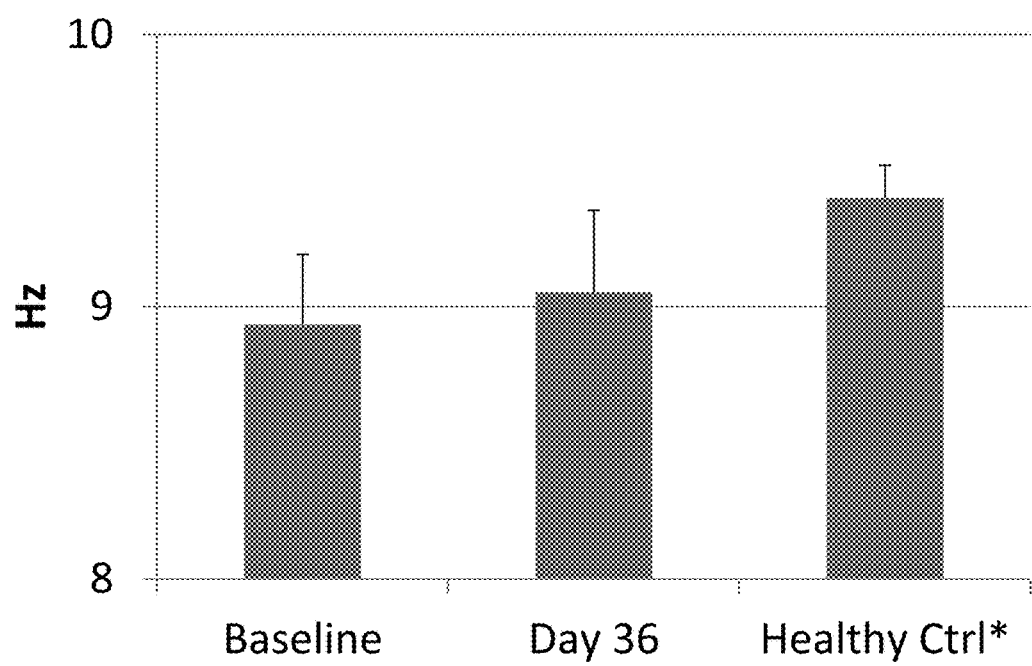
FIG. 8 illustrates electroencephalographic (EEG) peak alpha frequency (PAF) data for twelve patients at baseline and day 36 following the on-off-on ANAVEX2-73 dosing regimen, as compared to a healthy control group.
Figure 9:
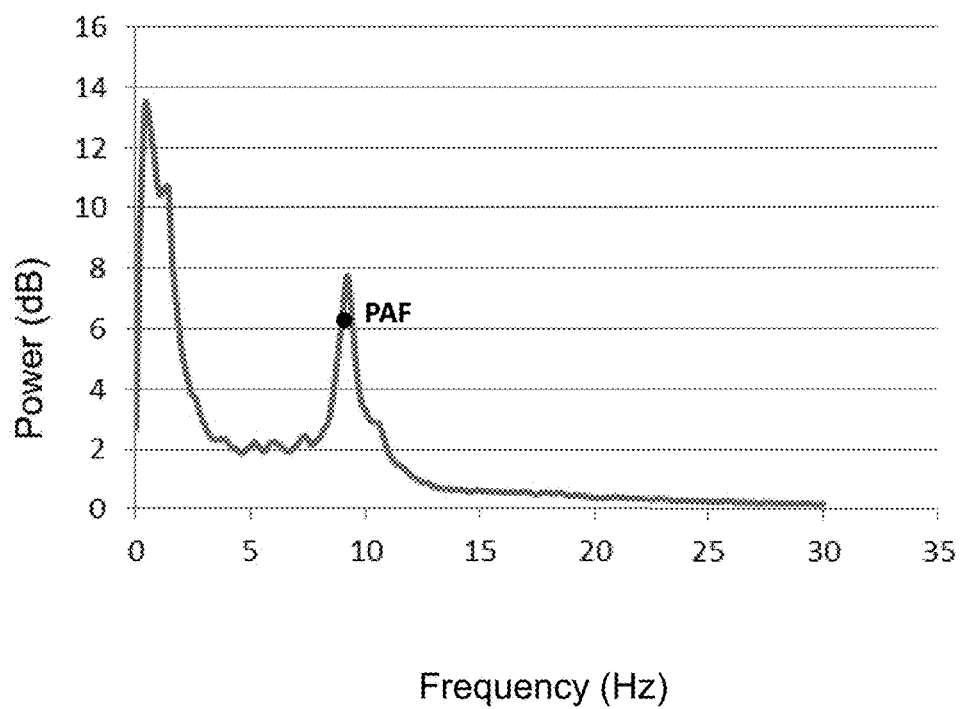
FIG. 9 illustrates an electroencephalographic (EEG) power spectrum indicating the peak alpha frequency (PAF).

FIG. 8 illustrates electroencephalographic (EEG) peak alpha frequency (PAF) data for twelve patients at baseline and day 36 following the on-off-on ANAVEX2-73 dosing regimen, as compared to a healthy control group. Electroencephalographic (EEG) peak alpha frequency (PAF), measured in Hz, is a distinctive individual "fingerprint" that has been correlated to cognitive performance and reflects a trait or state of cognitive preparedness. Patients with Alzheimer's disease have been found to have reduced PAF when compared to age-matched controls. PAF measures the discrete frequency with the highest magnitude within the alpha range. For example, FIG. 9 illustrates an electroencephalographic (EEG) power spectrum indicating the peak alpha frequency (PAF). As shown in FIG. 8, the measured PAF for subjects undergoing the ANAVEX2-73 dosage regimen was higher than the baseline measurement of PAF. FIG. 8 indicates that ANAVEX2-73 is able to shift PAF in subjects as compared to the measured PAF baseline. In addition, ANAVEX2-73 was found to improve the P300 signal in 10 out of the 12 patients (83%) studied.

The results for the twelve subject on-off-on dosing regimen of ANAVEX2-73, shown in FIGS. 5-9, were achieved without any dose optimization. Preliminary measured Mini Mental State Examination (MMSE) and Cogstate scale changes are consistent with the observed trend of the cognitive EEG/ERP effect. The safety profile of ANAVEX2-73 during Phase 2a trials appears consistent with the Phase 1 data. An additional 20 subjects will be studied during the remainder of the Phase 2a clinical trial. Phase 2b clinical trials, involving an additional 26-week extension of daily oral dosage administration of ANAVEX2-73 is on-going.

According to the present disclosure, ANAVEX2-73 can be administered according to an intermittent dosing schedule, in which a subject is administered ANAVEX2-73 for a period of days, followed by a period of days in which no ANAVEX2-73 is administered, before administration of ANAVEX2-73 is once again resumed. In some cases, the period of administration is of the same duration as the period of no administration. In other cases, the period of administration may be of a longer or shorter duration than the period of administration. In some cases, ANAVEX2-73 is administered according to an intermittent dosing regimen of at least two cycles, each cycle comprising (a) a dosing period during which a therapeutically effective amount of ANAVEX2-73 is administered to a patient and thereafter (b) a resting period. In one embodiment, the dosing period is for 1-12 days and the rest period is for 1-12 days. In other embodiments, the dosing period can be 1 day, 2 days, 3 days, 4 days, 5 days, 6 days, 7 days, 8 days, 9 days, 10 days, 11 days, 12 days, 13 days, or 14 days. In some embodiments, the resting period can be 1 day, 2 days, 3 days, 4 days, 5 days, 6 days, 7 days, 8 days, 9 days, 10 days, 11 days, 12 days, 13 days, or 14 days.

In some cases, the dosing period described herein can be in the range of a lower limit of about 1 day, 2 days, 3 days, 4 days, 5 days, 6 days, 7 days, 8 days, 9 days, 10 days, 11 days, 12 days, 13 days, and 14 days to an upper limit of about 28 days, 27 days, 26 days, 25 days, 24 days, 23 days, 22 days, 21 days, 20 days, 19, days, 18 days, 17 days, 16 days, 15 days, and 14 days. In some cases, the resting period described herein can be in the range of a lower limit of about 1 day, 2 days, 3 days, 4 days, 5 days, 6 days, 7 days, 8 days, 9 days, 10 days, 11 days, 12 days, 13 days, and 14 days to an upper limit of about 28 days, 27 days, 26 days, 25 days, 24 days, 23 days, 22 days, 21 days, 20 days, 19, days, 18 days, 17 days, 16 days, 15 days, and 14 days.

In one embodiment, the intermittent dosage schedule described herein comprises an oral dosage form comprising about 30 mg ANAVEX2-73. In another embodiment, the intermittent dosage schedule described herein comprises an oral dosage form comprising about 50 mg ANAVEX2-73. In another embodiment, the intermittent dosage schedule described herein comprises an oral dosage form comprising between about 30 mg and 50 mg ANAVEX2-73. In another embodiment, the intermittent dosage schedule described herein comprises an oral dosage form comprising between about 1 mg and 55 mg ANAVEX2-73.

In some cases the oral dosage form described herein can be in the range of a lower limit of about 1 mg, 5 mg, 10 mg, 15 mg, 20 mg, 25 mg, and 30 mg ANAVEX2-73 to an upper limit of about 60 mg, 55 mg, 50 mg, 45 mg, 40 mg, 35 mg, and 30 mg ANAVEX2-73.

In one embodiment, the intermittent dosage schedule described herein comprises intravenous administration of about 3 mg ANAVEX2-73. In another embodiment, the intermittent dosage schedule described herein comprises intravenous administration of about 5 mg ANAVEX2-73. In another embodiment, the intermittent dosage schedule described herein comprises intravenous administration of between about 3 mg and 5 mg ANAVEX2-73. In another embodiment, the intermittent dosage schedule described herein comprises intravenous administration of between about 1 mg and 10 mg ANAVEX2-73. In some cases the intravenous administration described herein can be in the range of a lower limit of about 1 mg, 2 mg, 3 mg, 4 mg, and 5 mg ANAVEX2-73 to an upper limit of about 10 mg, 9 mg, 8 mg, 7 mg, 6 mg, and 5 mg ANAVEX2-73.

All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or equivalently, "from approximately a to b," or, equivalently, "from approximately a-b") disclosed herein is to be understood to set forth every number and range encompassed within the broader range of values.

The compositions disclosed herein individually or in combination are employed in admixture with conventional excipients, i.e., pharmaceutically acceptable organic or inorganic carrier substances suitable for parenteral, enteral (e.g., oral or inhalation) or topical application which do not deleteriously react with the active compositions. Suitable pharmaceutically acceptable carriers include but are not limited to water, salt solutions, alcohols, gum arabic, vegetable oils, benzyl alcohols, polyethylene glycols, gelatin, carbohydrates such as lactose, amylose or starch, magnesium stearate, talc, titanium dioxide, silicic acid, viscous paraffin, perfume oil, fatty acid esters, hydroxyl methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with active compositions. They can also be combined where desired with other active agents, e.g., vitamins.

In some embodiments, dosage forms include instructions for the use of such compositions. For parenteral application, particularly are injectable, sterile solutions, preferably oily or aqueous solutions, as well as suspensions, emulsions, or implants, including suppositories. Ampules, vials, and injector cartridges are convenient unit dosages. "Unit dosage form" shall mean single administration entity. By way of example, a single tablet, capsule, dragee, or trochee, suppository, or syringe.

Also for parenteral application, particularly suitable are tablets, dragees, liquids, drops, suppositories, or capsules. A syrup, elixir, or the like can be used wherein a sweetened vehicle is employed. Sublingual and buccal forms are also noted.

Sustained or direct release compositions can be formulated, e.g., liposomes or those wherein the active component is protected with differentially degradable coatings, e.g., by microencapsulation, multiple coatings, etc. It is also possible to freeze-dry the new compositions and use the lyophilizates obtained, for example, for the preparation of products for injection.

EXAMPLES

The following examples show uses of ANAVEX2-73 in the treatment of patients with Alzheimer's disease or presenting with the early signs of Alzheimer's disease. The clinical determination that a patient may have Alzheimer's disease or is presenting with early signs of Alzheimer's disease is well known in the art. By way of example, the following references (and all publications cited herein) are incorporated by reference herein in their entireties: *Dementia: From Diagnosis to Management—A Functional Approach* 1$^{st}$ Edition, Psychology Press (Feb. 17, 2009); *Clinician's Guide to Psychological Assessment and Testing: With Forms and Templates for Effective Practice* 1$^{st}$ Edition, Springer Publishing Company (Sep. 18, 2012); *Neurodegener. Dis. Manag.* 5(3), 191-201 (2015); *Artif. Intell. Med.* 64(1), 59-74 (2015); *Clin. Chem.* 60(12), 1585-1586 (2014); and *Metabolism* 64(3 Suppl 1), S47-50 (2014).

Example 1

A 63 year-old male presents with early signs of Alzheimer's disease. He is orally administered a pharmaceutical composition containing 30 mg ANAVEX2-73 according to an intermittent dosing regimen where each cycle includes daily administration for 10 days (dosing period) followed by 10 days of no administration (resting period). The patient is administered 30 mg ANAVEX2-73 according to the intermittent dosing regimen for 6 months. His loss of cognitive function stabilizes during that period.

Example 2

A 58 year-old male presents with signs of early onset Alzheimer's disease. He is orally administered a pharmaceutical composition containing 50 mg ANAVEX2-73 according to an intermittent dosing regimen where each cycle includes daily administration for 10 days (dosing period) followed by 20 days of no administration (resting period). His loss of cognitive function stabilizes during that period.

Example 3

A 60 year-old female presents with signs of early onset Alzheimer's disease. She is administered 3 mg of ANAVEX2-73 intravenously according to an intermittent dosing regimen where each cycle includes daily administration for 5 days (dosing period) followed by 20 days of no administration (resting period) for one year. Her loss of cognitive function stabilizes during that period.

Example 4

A 55 year-old male presents with signs of early onset Alzheimer's disease. He is administered 5 mg of ANAVEX2-73 intravenously according to an intermittent dosing regimen where each cycle includes daily administration for 14 days (dosing period) followed by 7 days of no administration (resting period) for one year. His loss of cognitive function stabilizes during that period.

Example 5

A 64 year-old female presents with early signs of Alzheimer's disease. She is orally administered a pharmaceutical composition containing 50 mg ANAVEX2-73 according to an intermittent dosing regimen where each cycle includes daily administration for 14 days (dosing period) followed by 7 days of no administration (resting period). The patient is administered 50 mg ANAVEX2-73 according to the intermittent dosing regimen for 6 months. Her loss of cognitive function is stabilized during that period.

What is claimed is:

1. A pharmaceutical composition for the treatment of Alzheimer's disease comprising a therapeutically effective amount of tetrahydro-N,N-dimethyl-2,2-diphenyl-3-furanmethanamine hydrochloride (ANAVEX2-73), wherein the ANAVEX2-73 is a crystalline form of Anavex2-73 characterized by the powder X-ray diffraction (PXRD) pattern shown in FIG. 1.

2. The pharmaceutical composition according to claim 1, wherein the Alzheimer's disease is mild-to-moderate Alzheimer's disease.

3. The pharmaceutical composition according to claim 1, wherein the crystalline form of ANAVEX2-73 is characterized by the thermogravimetric analysis of FIG. 2a or FIG. 2b.

4. The pharmaceutical composition according to claim 1, wherein the crystalline form of ANAVEX2-73 is characterized by the differential scanning calorimetry analysis of FIG. 3a, 3b, or 3c.

5. The pharmaceutical composition according to claim 1, wherein the crystalline form of ANAVEX2-73 is characterized by the particle shapes as depicted in FIG. 4a, FIG. 4b, or FIG. 4c.

6. The pharmaceutical composition according to claim 1, wherein the crystalline form of ANAVEX2-73 is characterized by the particle sizes as depicted in FIG. 4a, FIG. 4b, or FIG. 4c.

7. The pharmaceutical composition according to claim 1, wherein the crystalline form of ANAVEX2-73 is characterized by a particle size of between 1 and 50 µm.

8. The pharmaceutical composition according to claim 1, wherein the therapeutically effective amount is about 1 mg to about 60 mg.

9. The pharmaceutical composition according to claim 1, wherein the therapeutically effective amount is about 30 mg to about 50 mg in an oral dosage form.

10. The pharmaceutical composition according to claim 1, wherein the therapeutically effective amount is about 3 mg to about 5 mg in an intravenous dosage form.

11. The pharmaceutical composition according to claim 1, further comprising at least one acetylcholinesterase inhibitor.

12. The pharmaceutical composition according to claim 1, wherein the at least one acetylcholinesterase inhibitor is selected from the group consisting of donepezil, galantamine, rivastigmine, or memantine.

13. A method of treating Alzheimer's disease in a subject comprising administering to the subject a therapeutically effective amount of a pharmaceutical composition according to claim 1; and wherein said pharmaceutical composition is administered according to an intermittent dosing regimen of at least two cycles, each cycle comprising (a) a dosing period during which a therapeutically effective amount of said pharmaceutical composition is administered to said patient and, thereafter, (b) a resting period.

14. The method according to claim 13, wherein the dosing period and the resting period are of the same duration.

15. The method according to claim 13, wherein the dosing period and the resting period are of different durations.

16. The method according to claim 13, wherein the dosing period and the resting period is in the range of a lower limit of about 10 days, 11 days, 12 days, 13 days, and 14 days to an upper limit of about 28 days, 27 days, 26 days, 25 days, 24 days, 23 days, 22 days, 21 days, 20 days, 19 days, 18 days, 17 days, 16 days, 15 days, and 14 days.

17. The method according to claim 13, wherein the dosing period is 12 days and the resting period is 12 days.

18. The method according to claim 13, wherein the therapeutically effective amount of said pharmaceutical composition is about 1 mg to about 60 mg.

19. The method according to claim 13, wherein the therapeutically effective amount of said pharmaceutical composition is about 30 mg to about 50 mg in an oral dosage form.

20. The method according to claim 13, wherein the therapeutically effective amount of said pharmaceutical composition is about 3 mg to about 5 mg in an intravenous dosage form.

21. The method according to claim 13, wherein the pharmaceutical composition is administered daily.

22. The method according to claim 17, wherein the pharmaceutical composition is administered for a period of at least 26 weeks.

23. The method according to claim 17, wherein the therapeutically effective amount of said pharmaceutical composition is about 1 mg to about 60 mg.

24. The method according to claim 17, wherein the therapeutically effective amount of said pharmaceutical composition is about 30 mg to about 50 mg in an oral dosage form.

25. The method according to claim 17, wherein the therapeutically effective amount of said pharmaceutical composition is about 3 mg to about 5 mg in an intravenous dosage form.

* * * * *